United States Patent [19]

Johnson et al.

[11] Patent Number: 4,806,275
[45] Date of Patent: Feb. 21, 1989

[54] IONIC DERIVATIVES OF ALKYL MONO AND POLYGLYCOSIDES

[75] Inventors: Donald L. Johnson, Muscatine, Iowa; Kenneth B. Moser, Decatur, Ill.; Vivian Valenty, Tempe, Ariz.

[73] Assignee: A. E. Staley Manufacturing Company, Decatur, Ill.

[21] Appl. No.: 86,990

[22] Filed: Aug. 19, 1987

Related U.S. Application Data

[63] Continuation-in-part of Ser. No. 904,143, Sep. 5, 1986.

[51] Int. Cl.$^4$ .................. B01F 17/02; C07H 15/10
[52] U.S. Cl. .................. 252/554; 252/174.17; 252/353; 252/551; 536/4.1; 536/115; 536/121; 536/122
[58] Field of Search .................. 252/8.55 D, 174.17, 252/174.18, 554; 536/4.1, 122, 115, 121

[56] References Cited

U.S. PATENT DOCUMENTS

| | | | |
|---|---|---|---|
| 1,951,784 | 3/1934 | Bertsch | 260/100 |
| 1,951,785 | 3/1934 | Bertsch | 260/100 |
| 2,049,758 | 8/1936 | Bertsch et al. | 260/210 |
| 2,356,565 | 8/1944 | Chwala | 260/210 |
| 3,737,426 | 6/1973 | Throckmorton et al. | 260/210 |
| 4,483,780 | 11/1984 | Llenado | 252/135 |
| 4,565,647 | 1/1986 | Llenado | 252/174.17 |
| 4,597,770 | 7/1986 | Forand et al. | 536/18.6 |
| 4,609,478 | 9/1986 | Egan | 536/4.1 |
| 4,675,392 | 6/1987 | Dahmen et al. | 536/17.6 |

OTHER PUBLICATIONS

Paper entitled Development of a New Dispersant Derived from Fatty Alcohol and Discussion of its Performance in Coal-Water Fuel Slurries.
Some Methods for the Purification of Sugar Sulfates by J. R. Turvey and M. J. Clancy, Nature, Feb. 21, 1959 (pp. 537 & 538).
New Biodegradable Surfactants Derived from Starch Preparation and Properties by Throckmorton et al., Tenside Detergents, Jan./Feb. 1973 (pp. 1-7).

Primary Examiner—Johnnie R. Brown
Assistant Examiner—Elli Peselev
Attorney, Agent, or Firm—Michael F. Campbell; Ernest G. Szoke; Wayne C. Jaeschke

[57] ABSTRACT

New anionic derivatives of mono and polyglycosides which are surface-active agents are described which anionic derivatives have the general formula

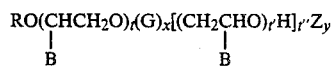

wherein
G is a glycosyl moiety which is derived from a reducing sugar selected from the group consisting of fructose, glucose, mannose, galactose, talose, gulose, allose, altrose, idose, arabinose, xylose, lyxose, ribose or mixtures thereof,
R is an alkyl group substituted at the reducing carbon of the reducing sugar from which the glycosyl moiety, G, is derived, said alkyl group being straight chain or branched chain having 6 to 30 carbon atoms, $x = 1$ to 10, at least one of the hydroxyl groups of at least one of the glycosyl moieties (or of a hydroxyalkyl group attached directly or indirectly to a hydroxyl group of said glycosyl moiety) has a Z group substituted in place of said hydroxyl group, Z is a substituent which is

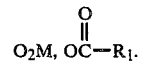

$O(CH_2)_pCO_2M$, $OSO_3M$, $O(CH_2)_pSo3_m$ and mixtures thereof and
$R_1 = (CH_2)_2CO_2M$ or $CH=CHCO_2M$, but $Z=O_2M$ only if Z is in place of a primary hydroxyl group in which case the primary hydroxyl-bearing carbon atom,
—$CH_2OH$, is oxidized to form a

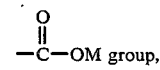

$M = H+$, an organic cation or inorganic cation,
$B = H-$, $CH_3-$ or $CH_3CH_2-$,
$t = 0$ to 10,
$t' = 0$ to 10,
$t'' = 0$ to $(3x+1)$,
$p = 0$ to 10, and
$y = 1$ to $3x+1$.

21 Claims, No Drawings

IONIC DERIVATIVES OF ALKYL MONO AND POLYGLYCOSIDES

This application is a continuation-in-part of application Ser. No. 06/904,143 which was filed on Sept. 5, 1986 still pending.

This invention relates to new ionic derivatives of alkyl polyglycosides and mixtures of alkyl mono and polyglycosides. More particularly, this invention relates to anionic derivatives of alkyl polyglycosides and mixtures of alkyl mono and polyglycosides. Alkyl polyglycosides are surface-active agents. Surface-active agents are divided into two broad classes according to their character in water, ionic and nonionic. Compounds belonging to the first class, the ionic surface-active agents, form ions in solution. Compounds of the second class, known as the nonionics, do not ionize but owe their solubility to the combined effect of a number of weak solubilizing groups such as ether linkages or hydroxyl groups in their molecules.

The general properties and behavior of surface-active agents are due to the dual character of the molecules of these substances. Their molecules are made up of two parts, a relatively large, elongated part, the hydrophobic group, and a small solubilizing, polar group, the hydrophilic group. The antagonism of these two portions of the molecule and the balance between them gives the compound its surface-active properties. The hydrophilic group exerts a solubilizing effect in generally polar liquids and tends to draw the entire molecule into solution; the hydrophobic group, on the other hand, because of its insolubility, has the effect of resisting this tendency. If a balance between the two groups exists, the substance neither dissolves completely nor remains completely undissolved, but concentrates at an interface such as a liquid-liquid or liquid-solid interface. In the case of a liquid-liquid interface with an aqueous phase, the molecules of the surface-active agent are so oriented that the hydrophilic groups are anchored in the aqueous phase and the hydrophobic groups project into the nonaqueous phase.

The ionic class of surface active agents is further subdivided in accordance with the way its members behave upon ionization. If, upon ionization, the ion containing the large hydrophobic group assumes a negative charge and becomes the anion, the compound is classified as an anionic surface-active agent. In this case the cation may be a simple metallic ion such as a sodium or potassium ion or the cation may be an ammonium radical such as ammonium or triethylammonium.

Alkyl polyglycosides are known nonionic surface-active agents which compositions have been known to be useful as detergents, gelling agents, lubricants, wetting agents, textile softeners and emulsifiers. U.S. Pat. Nos. 3,598,865; 3,707,535; 3,722,269; 3,839,318 and 4,536,317 all describe such nonionic glycosides. U.S. Pat. Nos. 4,483,787; 4,565,647 and 4,296,520 describe compositions which are mixtures of glycosides and anionic surfactants in an apparent attempt to benefit from the characteristics of the anionic compound.

Nonionic surface-active agents generally require hydrotopes to keep them in aqueous suspension with other surface-active agents, salts, builders and whitening agents which are used in cleaning compositions. Anionic surfactants do not. Moreover, it would be desirable to have an anionic surfactant which not only does not require a hydrotope to keep it in suspension, but which also is stable in an alkaline medium.

It is an object of this invention to provide new ionic derivatives of mono and polyalkylglycosides which are surface-active agents.

It is another object of this invention to provide new ionic mono and polyglycosides which do not require a hydrotope to keep them in aqueous suspension.

It is yet another object of this invention to provide new surface active agent combinations. These and other objects and advantages of the invention will become apparent from the following detailed description.

According to the invention new ionic compounds which are generally mixtures of are mono and polyglycosides have been discovered which compounds have the general formula

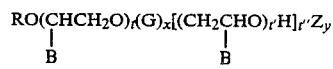

wherein
G is a glycosyl moiety which is selected from the group consisting of fructose, glucose, mannose, glactose, talose, gulose, allose, altrose, idose, arabinose, xylose, lyxose, ribose or mixtures thereof,
R is an aliphatic or aromatic hydrocarbon group substituted either directly or indirectly (i.e., through one or more

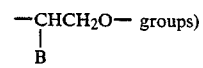

at the reducing carbon of the reducing sugar from which the glycosyl moiety, G, is derived which aliphatic or aromatic hydrocarbon group is a linear chain or is branched, open chain or cyclic and has 6 to 30 carbon atoms, $x = 1$ to 10, at least one of the hydroxyl groups of at least one of the glycosyl moieties (or of a hydroxyalkyl group attached directly or indirectly to a hydroxyl group of said glycosyl moiety) is substituted with a Z group in place thereof, $Z = O_2M$,

$O(CH_2)_pCO_2M$, $OSO_3M$, $O(CH_2)_pSO_3M$ and mixtures thereof and $R_1 = (CH_2)_2CO_2M$ or $CH=CHCO_2M$, but $Z=O_2M$ only if Z is in place of a primary hydroxyl group, and in that event it is to be understood that the primary hydroxyl-bearing carbon atom, $-CH_2OH$, has been oxidized to form a

$M=H+$ or an organic or inorganic cation such as an alkali metal, ammonium, monoethanolamine or calcium,
$B=H-$, $CH_3-$ or $CH_3CH_2-$,
$t=0$ to 10 t'=0 to 10,
t"=0 to (3x+1),
p=1 to 10, and
y=1 to 3x+1.

Preferably, no more than two Z ions or substituents are associated with any one glycosyl moiety and R is an alkyl group which is linear or branched having 6 to 30 carbon atoms. Moreover, M will preferably be H+ or an alkali metal such as sodium or potassium.

R is the aglycone group bonded through oxygen to the hemiacetal carbon, that is the carbon bonded to the oxygen forming a part of the glycosyl ring. One of the most common of the glycosides used in the invention as surface-active agents are alkyl glucosides (G is glucose). Glucosides have six membered rings with the alkyl aglycone R as follows at the $C_1$ position.

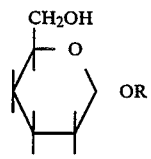

The degree of polymerization (D.P.) of the new ionic glycosides varies and is in the range of about 1 to 10 (x=1 to 10) and the polyglycosides of the invention usually exist as mixtures of varying degree of polymerization. Polyglycosides in these mixtures have a degree of polymerization as high as 10, but most of the polyglycosides in the mixtures have a degree of polymerization of 5 or less. Because the glycosides are often found as mixtures, x may be expressed as an average degree of polymerization (Av. D.P.) which includes fractional numbers. Recognizing that the glycosides used according to the invention are mixtures with varying degrees of polymerization, the average degree of polymerization of the polyglycosides of the invention is from about 1 to about 5. Preferably the average degree of polymerization, x, of the ionic glycoside products hereof is from about 1 to about 2, and indeed, the benefits of the ionic derivatization of interest herein have been found to be particularly pronounced and noteworthy in those instances wherein the average degree of polymerization, x, of the glycoside product of concern is in the range of from about 1 to about 1.7, (preferably from about 1 to about 1.5, more preferably from about 1 to about 1.4 and especially from about 1 to about 1.3). The group R at the reducing carbon position (i.e, the $C_1$ position in the case of aldosides such as glucosides and the $C_2$ position in the case of the ketosides such as fructosides) of the glycoside in most surface-active applications is an alkyl group which is straight chain or branched having 8 to 18 carbon atoms.

The number of ions on the glycosyl groups is limited by the amount of charges created by putting ions on the glycosyl group, and by stearic considerations including the position at which the glycosyl groups are bonded to one another. For example, if the glycosyl group is a six-membered ring, it is more likely that if the rings are bonded at the 1, 4 or 1, 3 positions, two ions can be more easily substituted onto the glycosyl ring than if the rings were bonded by linkages at the 1, 6 or 1, 2 positions of the glycosyl rings. In the latter case, it is more likely that a maximum of only one ion or Z substituent will be present on each such glycosyl moiety. Hence, while the number of Z substituents overall (y) can theoretically be as much as 3x+1 per glycoside molecule, the value of y will, by virtue of the considerations described above, typically not exceed 2x+1 per glycoside molecule and, more preferably, the average extent of Z substitution on the individual glycosyl groups of the compounds of the invention is about 1.5 or less. Accordingly, the value of y in the ionic glycoside formula stated above is more typically in the range of from 1 to 2x+1 and is preferably in the range of from 1 to about 1.5x+1.

In certain especially preferred embodiments hereof, the ionic glycoside derivatives of interest contain an average of only 1 to 2 Z substituents per glycoside molecule (i.e., y is, on average, from 1 to about 2 in the above presented structural formula and is preferably from 1 to about 1.5 on average) and, in such instances, the average Z substituent content on a per glycosyl moiety basis is typically from about 0.1 to about 2, preferably from about 0.2 to about 1.5, more preferably from about 0.2 to about 1.3 and most preferably from about 0.3 to about 1.

The various glycoside and polyglycoside compounds including alkoxylated glycosides and processes for making them are disclosed in U.S. Pat. Nos. 2,974,134; 3,219,656; 3,598,865; 3,640,998; 3,707,535; 3,772,269; 3,839,318; 3,974,138; 4,223,129 and 4,528,106. All of the latter patents are incorporated by reference herein.

The sulfate compounds of the invention, e.g., Z=O-SO₃M, may be made by reacting an alkyl polyglycoside or an alkyl mono and polyglycoside mixture with sulfur trioxide. The sulfonic acid and sulfonate salt compounds of the invention, e.g., $O(CH_2)_pSO_3M$, may be made by the reaction of cyclic compounds such as

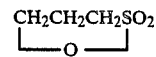

with polyglycosides or mono and polyglycoside mixtures. The oxy carboxylic acid compounds of the invention, e.g., $O(CH_2)_pCO_2M$, of the invention can be made by the reaction of halogen substituted carboxylic acids, e.g., halo $(CH_2)_pCO_2M$, with polyglycosides or mono and polyglycoside mixtures. The succinic and maleic compounds of the invention may be made by the reaction of succinic anhydride and maleic anhydride with polyglycosides or mono and polyglycoside mixtures. The carboxylate compounds of the invention that are made via oxidation are restricted to conversion of primary hydroxyl groups on the glycosyl moiety to carboxylate groups. For example, in respect to a glucoside there is one primary hydroxyl group on the glycosyl moiety, for example.

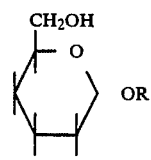

According to the invention where the compositions are carboxylated, the primary hydroxyl group may be converted to $CO_2H$ which in the case of glucose would make the glycosyl moiety:

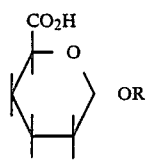

Hence, according to the invention, the glycosyl moiety of the compounds of the invention either has the primary hydroxyl group or, in lieu of such a hydroxyl group, the glycosyl moiety is substituted with a carboxyl group. The carboxylated glycosyl moiety is obtained by oxidizing the primary hydroxyl group as described in connection with glucose and monoglycosides in *Salam ad Isbell, Carbohydrate Research*, 101 (1982) 255–261 and *Bollenback, Methyl Glucoside*, pp 144–149 Academic Press, Inc. (1958).

Although utilitarian by themselves as anionic surface active agents, the compounds of the invention may be used in combination with other surface active agents, including alkyl polyglycosides, and in combinations such as those disclosed in U.S. Pat. Nos. 4,396,520; 4,483,779; 4,483,780; 4,493,773, 4,536,318; 4,536,319; and 4,565,647 all of which are incorporated by reference herein. As to the referenced patents, the compounds of the invention may be used as an addition to the various disclosed combinations or in lieu of the alkyl polyglycoside or alkylpolysaccharides or the anionic components described in the referenced patents.

In certain especially preferred embodiments, the anionic glycoside surfactant derivatives hereof are utilized in combination with nonionic counterparts thereof (i.e., in combination with nonionic glycoside surfactants corresponding to the formula

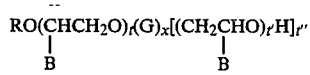

wherein R, B, t, G, x, t' and t" are as hereinbefore described). In such instances, the weight ratio of the anionic glycoside surfactant derivative to the nonionic glycoside surfactant component will typically be in the range of from about 20:1 to about 1:100 and will preferably be in the range of from about 10:1 to about 1:50 (more preferably from about 4:1 to about 1:20, especially from about 3:1 to about 1:10 and most preferably from about 2:1 to about 1:5).

The indicated type of combined anionic glycoside surfactant/nonionic glycoside surfactant compositions are illustrated within the following working examples in the form of those compositions wherein the average degree of anionic group, Z, substitution is indicated as being an average value of less than one on a per glycoside molecule basis. In such compositions, the indicated less-than-one, fractional value of y plainly reflects the fact that said compositions necessarily contain a mixture of both derivatized anionic glycoside surfactant molecules (i.e., in which y is, by definition, a value of 1 or more) and non-derivatized, nonionic glycoside surfactant molecules (i.e., in which y is zero, reflecting a lack of Z substituents on those particular glycoside surfactant molecules). Particularly preferred mixed anionic glycoside plus nonionic glycoside surfactant compositions hereof are those which contain an average of from about 0.05 to about 0.75 (preferably from about 0.1 to about 0.6 and more preferably from about 0.1 to about 0.5) anionic substituents (i.e., Z groups) per glycoside surfactant molecule within said compositions, said average being taken, of course, over the combined total of both anionic and nonionic (i.e., y=o) glycoside surfactant molecules.

Examples of the compounds of the invention are made as follows.

EXAMPLE 1

Preparation of $CH_3(CH_2)_{11}O(glucose)_{1.3}(SO_4Na)_1$ 84.4 grams of $CH_3(CH_2)_{11}$ glucoside, which is an alkyl polyglucoside mixture which has an average degree of polymerization of 1.3, is dissolved with heat using a water bath into 300 ml dimethyl formamide. The solution is allowed to cool until the alkyl polyglycoside mixtures starts to precipitate. Sulfur trioxide-trimethylamine compex, $SO_3.(CH_3)_3N$ (55.1 g.) is slowly added with stirring to the solution of alkyl polyglucoside mixture in dimethyl formamide. The mixture is stirred at room temperature for 24 hours. The pH is adjusted to 7.4 with 0.5N methanolic NaOH before removing the solvent by means of a rotary evaporator which will yield the unpurified $C_{12}$ product which has a generalized structural formula of

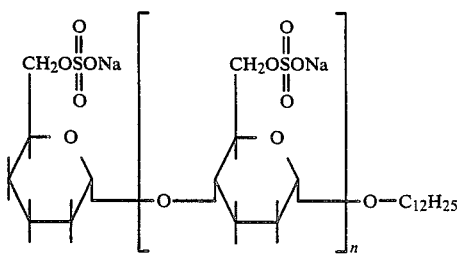

and which has an average degree of polymerization of 1.3 and a substitution of about one $SO_4Na$ group per glycosyl group. The residual syrup is poured into an evaporating dish and dried further in a vacuum oven at 40°–50° C. This residue gives a positive methylene blue test for an anionic surfactant. Increased water solubility of the product over the starting material is also evidence of sulfate incorporation. The product has surface tension comparable to and interfacial tension higher than those of the starting alkyl polyglucoside mixture.

EXAMPLE 2

Preparation of Succinyl Carboxylated Alkyl Polyglucoside

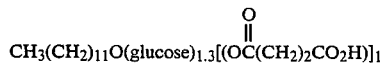

60.0 grams of $CH_3(CH_2)_{11}$ glucoside, which is an alkyl glucoside mixture which has an average degree of polymerization of 1.3 or a degree of polymerization of 1 to about 5, is dissolved in 550 ml of hexane and refluxed at about 61° C. until about 8.5 ml. of water is produced. After the yielding of water, 26.1 grams of succinic anhydride is charged into the reaction vessel after which the glucoside, anhydride and hexane reaction mixture is refluxed for 2 hours to yield the succinyl carboyxylated alkyl polyglucoside mixture which has the general structural formula of

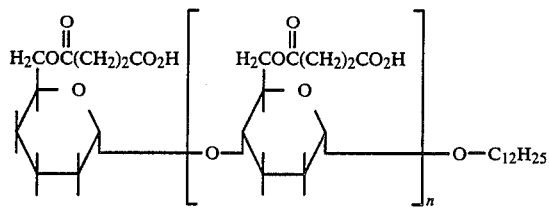

and which has an average degree of polymerization of 1.3 and a substitution of about one

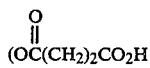

group per glycosyl moiety.

EXAMPLE 3

Preparation of Succinyl Carboxylated Alkyl Polyglucoside

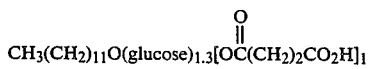

60.0 grams of $CH_3(CH_2)_{11}$ glucoside having an average degree of polymerization of 1.3 or a degree of polymerization of 1 to about 5 is dissolved in 500 ml of hexane and is refluxed at 61° C. until no water comes off of the refluxing mixture (about 16.5 ml water). Succinic acid (30.9 g) is charged into the glycoside/hexane mixture. The anhydride/polyglycoside/hexane reaction mixture then is refluxed until no water comes off the reaction (about 3.5 ml $H_2O$). 25.5 mg of dibutyl tin oxide catalyst available commercially under the name of FASCAT 4201, is charged into the reaction mixture when no additional water comes off, esterification is indicated, and 25.5 mg more catalyst is added. Sufficient xylene and heat are added to raise the reaction temperature to 90° C., then to 140° C. with refluxing to yield $$CH_3(CH_2)_{11}O(glucose)_{1.3}[OC(CH_2)_2(CO_2H]_1$$

EXAMPLE 4

Preparation of Carboxylated Alkyl Polyglucoside with Maleic Anhydride

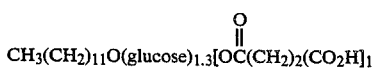

600 ml of water is charged into a 2 L three-necked round bottom flask. 176 grams of $CH_3(CH_2)_{11}$ glucoside having an average degree of polymerization of 1.3 is charged into the water with agitation with 86 grams of maleic anhydride and 78 grams of $Ca(OH)_2$ then being charged into the reaction mixture which is heated to 85°–90° C. and held at that temperature for 2 hours. The reaction is then cooled and filtered with methanol yielding a calcium salt. The calcium salt is reacted with the $Na_2CO_3$ by suspending the calcium salt in water (400 ml) at 80° C., adding anhydrous $Na_2CO_3$, and agitating the mixture for 25 minutes at about 80° C. Upon cooling $CaCO_3$ is filtered off. The resulting solution is triturated with methanol then filtered yielding a filtrate which is

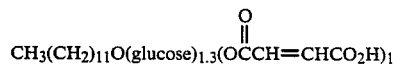

which has a general structural formula of

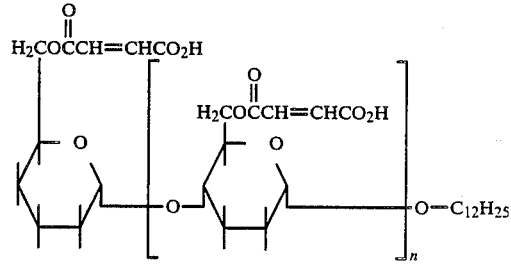

an average degree of polymerization of 1.3, and a substitution of about one $O_2CCH=CHCO_2H$ groups per glucosyl moiety.

EXAMPLE 5

Preparation of $CH_3(CH_2)_{11}O(glucose)_{1.3}(SO_4NA)_1$

Sulfur trioxide-trimethylamine complex (56.2 g) is slowly added with stirring to a solution of $CH_3(CH_2)_{11}O$ glucoside (84.8 g.) in 400 ml dimethylformamide. The mixture is stirred at room temperature for 19 hours (under nitrogen blanket). The pH is adjusted to 7.2 with 1N methanolic sodium hydroxide before removing the solvent under reduced pressure. The residual syrup is poured into evaporating dish and further dried in a vacuum oven at 65°–75° C. at 27 in. Hg to yield the above described sulfated $C_{12}$ glucoside.

Tests

Surface Tension and Interfacial Surface Tension

The ability of various compounds to act as anionic surfactants was measured with data as to the surface tensions and interfacial tensions of aqueous solutions of the compounds at a concentration of 300 ppm.

Surface tension was measured as the force necessary to pull a metal ring from the surface of a liquid. In conducting the surface tension test a Cenco-du Nouy Tensiometer, No. 70545, forceps, a bubble level, a bunsen burner, and a set of weights, 100–1000 mg in 100 mg increments are used.

The tensiometer is calibrated by inserting the ring into the lower end of the arm and leveling the sample table with the level and adjusting the leveling screws. A small strip of paper is placed on the ring to serve as a platform. The adjusting knob is turned so that the pointer and its mirror image are in line with the reference line. The dial 0.1 division is read for the zero reading. A 100 mg weight is placed on the paper with adjustment and reading as before. This is repeated, adding 100 mg each time until 1000 mg has been added. From each of the readings with the weight the zero reading is subtracted. This gives the experimental force P in mN/m. The true force P for each mass is calculated using:

$$P = M^*g/C2^*C.$$

where

M=mass in grams
g=980.1 cm/s**2 (Springfield)
C=circumference of the ring in centimeters.

The true force (y) is regressed against the experimental results (X) and the slope, a, and the intercept, b, are recorded.

After calibration the ring which is handled only with forceps is cleaned by heating it momentarily to a dull red in the oxidizing portion (just above the inner cone) of the flame of the Bunsen burner. The ring is inserted into the lower end of the arm of the tensiometer. The adjusting knob is released and turned so that the pointer and its mirror image are in line with the reference line. The zero of the vernier is adjusted opposite zero on the dial. The temperature of the sample is adjusted to 25° C. and the sample is then placed in a clean container and the entire sample table assembly is raised until the ring is immersed approximately 5 mm. Torsion is slowly increased by turning the adjusting knob to increase the reading on the side of the dial with the black numbers. When the film breaks, the dial is read to the nearest 0.1 division. The determinations are repeated until three consecutive readings within 1 dyne/cm are obtained and the three readings are averaged to give P' in mN/m. The corrected force, P, is calculated from P':

$$P = a*P' + b,$$

where
a=slope determined in calibration
b=intercept determined in calibration
P'=force determined as above.

The correction factor, F is calculated:

$$F = 0.7250 + ((0.01452*P/(C*C*(D-d))) + 0.04534 - (1.679/(R/r)))**\frac{1}{2}$$

where
P=corrected force
C=circumference of ring, cm
D=density of sample g/cm$^3$
d=density of saturated air, which is so small that it can usually be ignored
R=radius of ring cm
r=radius of wire, cm.

Surface tension is calculated by the following formula:

$$S(mN/m) = P*F.$$

Interfacial tension is a measure of molecular attractive forces between unlike molecules. It is applicable to liquids which are immiscible. In conducting the interfacial tension test, a Cenco-due Nouy Interfacial Tensiometer, No. 70540, forceps, a bubble level, a Bunsen burner and a teflon sample container, 75 mm tall, 105 mm diameter are used.

The tensiometer is calibrated by inserting the ring into the lower end of the arm and using the level to level the sample table. A small strip of paper on the ring serves as a platform and the adjusting knob is turned so that the pointer and its mirror image are in line with the reference line. The dial is read for the zero reading. An accurately known mass which is 0.5–0.8 g is placed on the paper and the adjusting knob is adjusted as before. The first reading is subtracted from the second reading, this difference is the experimental force p in mN/m.

Once the tensiometer is calibrated, the ring which is handled only with forceps is cleaned with the appropriate solvent, allowed to dry, and heated momentarily to a dull red in the oxidizing portion of the flame of the Bunsen burner. The ring is inserted into the lower end of the arm of the tensiometer. The adjusting knob is released and turned so that the pointer and its mirror image are in line with the reference. The zero of the vernier is adjusted to coincide exactly with the zero on the dial. The temperature of the liquids is adjusted to 25° C. The ring should move from the aqueous to the nonaqueous liquid. After increasing the torsion in the tensiometer the ring breaks through the interface of the liquids and the force to break through is measured. The interfacial tension(s) is calculated from this force (p) and correction factor (F).

$$S(mN/m) = p \times F$$

$$F = 0.7250 + ((0.01452*P/(C*C*(D-d))) + 0.04534 - (1.679/(R/r)))**\frac{1}{2}$$

where
P=corrected force, mN/m
D=density of lower layer, g/cm**3
d=density of upper layer, g/cm**3
R=radius of ring, cm
r=radius of wire, cm.

TABLE I

| | | Surface Tension (dynes/cm) | Interfacial Tension (dynes/cm) | AV. DP |
|---|---|---|---|---|
| A. | Maleic substituted C$_{12}$ alkyl polyglucoside; the ratio of moles of maleic anhydride reacted with moles of glucosyl moiety is about 1.0 | 69.3 | 10.4 | 1.3 |
| B. | C$_{12}$ alkyl polyglucoside with a carboxylate degree of substitution of about 1 per glucosyl moiety | 37.3 | 13.6 | 1.3 |
| C. | Sulphate substituted alkyl polyglucoside; the ratio of moles of SO$_3$ reacted per mole of glucosyl moiety is 1.1 | 68.9 | 20.6 | 2 to 3.5 |
| D. | Sulfate substituted C$_{12}$ alkyl polyglucoside; the ratio of moles of SO$_3$ reacted per mole of glucosyl moiety is 1.1 | 67.9 | 21.6 | 2 to 3.5 |
| E. | Sulfate substituted C$_{12}$ alkyl polyglucoside; the ratio of moles of SO$_3$ reacted per mole of glucosyl moiety is 1.1. | 24.5 | 6.44 | 1.3 |
| F. | Sulfate substituted C$_{12}$ alkyl polyglucoside; the ratio of moles of SO$_3$ reacted per mole of glucosyl moiety is 0.4. | 24.4 | 4.50 | 1.3 |
| | Acetone soluble C$_{12}$ alkyl polyglucoside with D.P. = 1.3 (Control) | 24.4 | 3.45 | |

Emulsion Separation Time

The ability of the anionic surfactants of the invention to act as emulsifying agents was measured by measuring and comparing emulsion separation times of aqueous solutions of the compounds of the invention. The test was conducted by measuring how long various solvents separated from water.

A known amount of surfactant is weighed into a stoppered cylinder. Solvent and distilled water are added. The cylinder is inverted 30 times within a 30 second time period. Then it is allowed to stand at room temperature. The ml separation is read at 5, 15, 30, 60, 120 and 180 minutes.

into the cylinder with the 50 ml of solution. The mm of foam is read after the initial solution drop and after 5 minutes.

The hand dishwashing test is to evaluate the performance of a liquid hand dishwashing detergent. The evaluation includes preparing soil comprising 37.5% by weight Crisco shortening, 12.5% by weight egg powder and 50% by weight tap water. Terry cloth $1 \times 1\frac{1}{2}$ inch swatches are soiled with 1.0 g. of the soil. An 8% aqueous solution of the wetting agent is prepared for addition to buckets of a Terg-o-Tometer having sufficient water which after the addition yield a 0.25% solution of

TABLE II

| | | Emulsion Separation vs. Time | | | | | | |
|---|---|---|---|---|---|---|---|---|
| | | SOLN Conc. | PERCENT SEPARATION @ TIME, MINS. | | | | | |
| SURFACTANT | SOLN pH | % by wt. | 5 | 15 | 30 | 60 | 120 | 180 |
| E. of Table I | 1.5 | 2% | 30 | 50 | 65 | 30 | 30 | 80 |
| | | 4% | 10 | 20 | 35 | 45 | 60 | 75 |
| | | 6% | 5 | 25 | 45 | 60 | 60 | 60 |
| F. of Table I | 1.4 | 2% | 5 | 10 | 30 | 40 | 40 | — |
| | | 4% | 5 | 10 | 20 | 30 | 40 | — |
| | | 6% | SL* | 5 | 10 | 20 | 30 | — |
| Sulfated alkyl polyglucoside | 1.8 | 2% | 30 | 50 | 65 | 70 | 80 | 80 |
| | | 4% | 30 | 45 | 60 | 70 | 80 | 80 |
| | | 6% | 30 | 40 | 60 | 70 | 80 | 80 |
| E. of Table I | 7.4 | 1.9% | 10 | 30 | 40 | 50 | 60 | — |
| | | 3.8% | 15 | 40 | 60 | 65 | 80 | 00 |
| | | 5.7% | 10 | 30 | 40 | 50 | 60 | — |
| F. of Table I | 7.0 | 1.9% | None | 25 | 45 | 50 | 60 | — |
| | | 3.9% | None | None | 40 | 50 | 60 | — |
| | | 5.8% | None | None | 40 | 40 | 50 | — |
| Example 2 surfactant | 6.5 | 1.9% | 70 | 80 | 90 | 90 | 90 | — |
| | | 3.7% | 10 | 20 | 40 | 50 | 60 | — |
| | | 5.6% | 10 | 20 | 40 | 50 | 60 | — |
| Example 2 surfactant | 8.4 | 2.0% | 20 | 40 | 60 | 65 | 80 | — |
| | | 3.9% | 20 | 40 | 50 | 65 | 80 | — |
| | | 5.9% | 20 | 40 | 50 | 65 | 80 | — |

*SL = Slight

The effect of the degree of sulfation of an alkyl polyglycoside was measured by sulfating a polyglucoside having an average degree of polymerization of 1.4 and an aglycone which is a $C_{12}$ to $C_{13}$ alkyl group. The degree of sulfation of the alkyl polyglucoside was increased by using the same reaction conditions and stoichiometrically increasing the sulfate reactant relative to alkyl polyglucoside such that more moles of sulfate per mole of polyglucoside were reacted with and substituted onto the polyglucoside. An unsulfated control A also was included in the tests. The tests on the effect of sulfation were: The Draves wetting test, Ross Miles foam test, a laundry cleaning test and hand dishwashing test.

The Draves wetting test consists of measuring the time required for a 5 g. skein of gray cotton yarn to sink in a solution of the wetting agent. A small hook of copper wire weighing 3 g. is hooked through one end of the folded skein. To the other end of the wire hook, a flat lead disk weighing about 40 g. is attached by means of a fine string. A 0.1% solution of the wetting agent is placed in a 500-ml. graduate and the skein with attached hook and sinker is allowed to drop into the solution and the stop watch started. The dry skein is at first buoyed up, but as the solution penetrates the yarn and it becomes wet, it sinks under the weight of the wire hook. The time is read just as the lower end of the hook touches the lead weight.

The Ross Miles foam test is conducted using a Ross Miles foam apparatus and an aqueous test solution having 0.1% of the surface active agent being tested. 50 ml of the test solution is put into the cylinder of the Ross Miles apparatus and 200 ml is dropped from a pipette the surface active agent. The solution in the buckets is agitated at 75 rpm, the agitation stopped and the soiled swatches are added one by one to the buckets until 50% of the surface foam on each bucket has disappeared. An average of two runs in terms of grams of soil needed to reduce the foam is reported.

A Tergotometer laundry cleaning detergency test measures the cleaning ability of surface active agents. A six station Terg-o-Tometer, Model #7243-S, from the U.S. Testing Company, Hoboken, N.J. and a Gardner digital colorimeter, Model XL-10, from Gardner Laboratory, Inc., Bethesda, Md. are used in the test. In the test a hard water stock solution is prepared by dissolving 29.6 g $MgSO_4.7H_2O$ and 26.4 g. $CaCl_2, 2H_2O$ in 15 liters distilled water. The heater of the Terg-o-Tometer is turned on and water bath temperature is adjusted to approximately 105°–110° F. Each of the six beakers of the Terg-o-Tometer are filled with 940 ml distilled water plus 60 ml synthetic hard water. When the water in the beakers reaches 105°–110° F., sufficient surface active agent to form a 0.25% solution is added to the beakers which are agitated for 30 seconds to dissolve the sample. Three each Dacron/cotton and cotton soiled swatches from Scientific Services, Oakland, N.J. are added to each beaker. The swatches are stirred in the solution for 15 minutes. At the end of the wash cycle, swatches are removed and squeezed, then rinsed in a large beaker (4000 ml) of tap water at approximately 100° F. for five minutes. The swatches are then squeezed to remove excess water. After removal of the excess water the swatches are dried in a clothes dryer for 15 minutes then ironed. The reflectance of the soiled swatches at 2 degrees illumination before and after washing are read and compared with the detergency units removed from the swatches being the differences in reflectances.

The effect of sulfation on the results of these various tests is shown in Table III.

TABLE III

Effect of Sulfating $C_{12-13}$ Nonionic Alkyl Polyglucoside Having an Average Degree of Polymerization of 1.4

|  | Unmodified Alkyl Poly-Glucoside Control A | B | C | D | E | F | Linear* Alkyl Sulfonate | Linear* Alkyl Ethoxylate |
|---|---|---|---|---|---|---|---|---|
| Moles Sulfate/ Reacted Alkyl Polyglucoside | 0 | 0.25 | 0.50 | 1.0 | 1.5 | 2.0 |  |  |
| 0.1% Draves Sink Time (Sec.) | 39 | 22 | 35 | 1 Min. 40 Sec. | 14 Min. | 60 Min. | 8 | 12 |
| 0.1% Ross Miles Foam - 75% |  |  |  |  |  |  |  |  |
| 0 Min. | 55 | 130 | 130 | 125 | 113 | 115 | 158 | 81 |
| 5 Min. | 55 | 125 | 125 | 122 | 110 | 107 | 152 | 76 |
| 0.25% Detergency Test in detergency units removed | 17.7 | 17.7 | 16.5 | 15.9 | — | 11.6 |  |  |
| Hand Dishwashing Soil Test | 9 | 8 | — | 6 | — | — |  |  |

*A linear alkyl sulfonate in the form of Biosoft D-62 which is a $C_{12}$ sodium benzene sulfonate from Stepan Chemical Company and a linear alkyl ethoxylate in the form of Neodol 25-7 from Shell Chemical Company which is $C_{12-15}$ ethoxylated alcohol (a reaction product of the alcohol with seven moles of ethylene oxide) were included in some of the tests for comparative purposes to compare the compositions of the invention with known ionic and nonionic surface active agents.

It should be understood that while certain preferred embodiments of the present invention have been illustrated and described, various modifications thereof will become apparent to those skilled in the art. Accordingly, the scope of the present invention should be defined by the appended claims and equivalents thereof.

Various features are set forth in the following claims.

What is claimed is:

1. Compounds which have the formula:

$$RO(CHCH_2O)_t(G)_x[(CH_2CHO)_{t'}H]_{t''}Z_y$$
$$\phantom{RO(}|\phantom{CHCH_2O)_t(G)_x[(CH_2CHO}|$$
$$\phantom{RO(CHCH_2O)}B\phantom{)_t(G)_x[(CH_2CHO)_{t'}H]_{t''}}B$$

wherein
G is a glycosyl moiety which is selected from the group consisting of fructose, glucose, mannose, galactose, talose, gulose, allose, altrose, idose, arabinose, xylose, lyxose, ribose or mixtures thereof,
R is bonded through an oxygen atom either directly or indirectly through one or more $$-CHCH_2O-\text{groups}$$
$$\phantom{-CHCH_2O}|$$
$$\phantom{-CHCH_2O-}B$$

to the reducing carbon of the reducing sugar from which the glycosyl moiety, G, is derived and is an alkyl group which is a straight chain or is branched having 8 to 18 carbon atoms, x = 1 to 10, at least one of the hydroxyl groups of at least one of the glycosyl moieties or of a hydroxyalkyl group attached directly or indirectly to a hydroxyl group of said glycosyl moiety is substituted with a Z group in place thereof, $Z = O_2M$, $$\overset{O}{\underset{\|}{OC}}-R_1,$$

$O(CH_2)_pCO_2M$, $O(CH_2)_pSO_3M$ and mixtures thereof and $R_1 = (CH_2)_2CO_2M$ or $CH=CHCO_2M$; $Z=O_2M$ only when Z is in place of a primary hydroxyl group and in that event the primary hydroxyl-bearing carbon atoms, $-CH_2OH$, is oxidized to form a $$\overset{O}{\underset{\|}{-C}}-OM \text{ group}$$

$M = H+$, an organic cation or inorganc cation,
$B = H-$, $CH_3-$ or $CH_3CH_2-$,
$t = 0$ to 10,
$t' = 0$ to 10,
$t'' = 0$ to $(3x+1)$,
$p = 1$ to 10, and
$y = 1$ to $3x+1$.

2. Compounds as recited in claim 1 wherein no more than two Z substituents are associated with one glycosyl moiety.

3. Compounds as recited in claim 2 wherein $M=H+$, an alkali metal or ammonium ion.

4. Compounds as recited in claim 3 wherein G is glucose.

5. Compounds as recited in claim 3 wherein the compounds have an average degree of polymerization, x, in the range of about 1 to about 5.

6. Compounds as recited in claim 3 wherein y has an average value of from about 1 to about 1.5.

7. Compounds as recited in claim 3 wherein t, t' and $t'' = 0$.

8. Compounds as recited in claim 7 wherein the compounds have an average degree of polymerization, x, in the range of about 1 to about 5.

9. Compounds as recited in claim 7 wherein y has an average value of from 1 to ablut 1.5.

10. Compounds as recited in claim 7 wherein Z=O₂M in place of a primary hydroxyl group and wherein M=H+ or an alkali metal or ammonium ion.

11. Compounds as recited in claim 7 wherein Z=

and wherein $R_1=(CH_2)_2CO_2M$ or $CH=CHCO_2M$ and M is H+ or an alkali metal or amonium ion.

12. Compounds as recited in claim 7 wherein $Z=O(CH_2)_pCO_2M$; p=1 to 10; and M=H+ or an alkali metal or ammonium ion.

13. Compounds as recited in claim 7 wherein $Z=O(CH_2)_pSO_3M$; p=1 to 10; and M=H+ or an alkali metal or ammonium ion.

14. Compounds as recited in claim 10 wherein y has an average value of from 1 to about 1.5.

15. Compounds as recited in claim 11 wherein y has an average value of from 1 to about 1.5.

16. Compounds as recited in claim 12 wherein y has an average value of from 1 to about 1.5.

17. Compounds as recited in claim 13 wherein y has an average value of from 1 to about 1.5.

18. A composition which comprises a mixture of an anionic glycoside surfactant in accordance with claim 1 in combination with one or more nonionic glycoside surfactants of the formula:

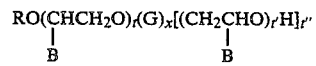

wherein R, B, t, G, x, t' and t" are as defined in claim 1 and wherein the weight ratio of said anionic glycoside surfactant to said nonionic glycoside surfactant within said mixture is from about 20:1 to about 1:100.

19. The composition of claim 18 wherein the value of x for both the anionic and the nonionic glycoside surfactant ingredient is from 1 to about 2.

20. The composition of claim 19 wherein the average value of y in the anionic glycoside surfactant ingredient is from 1 to about 1.5.

21. The composition of claim 20 wherein the anionic glycoside surfactant to nonionic glycoside surfactant weight ratio is from about 3:1 to about 1:10.

* * * * *